United States Patent [19]

Ferrara

[11] 4,399,103
[45] Aug. 16, 1983

[54] BLOOD DISPENSER DEVICE

[76] Inventor: Louis T. Ferrara, 2988 Ave. T, Brooklyn, N.Y. 11229

[21] Appl. No.: 229,120

[22] Filed: Jan. 28, 1981

[51] Int. Cl.³ .................. G01N 1/00; B65D 35/28
[52] U.S. Cl. ........................... 422/100; 73/864.14; 73/864.41; 222/101; 436/180; 215/32
[58] Field of Search ........... 73/864.11, 864.14, 864.15, 73/864.12, 864.16, 864.17, 864.18, 864.41; 422/100, 81, 82; 128/214 R; 222/101 X, 95, 82; 215/32 X; 7/158

[56] References Cited

U.S. PATENT DOCUMENTS

| | | | |
|---|---|---|---|
| 2,681,504 | 6/1954 | Fox | 7/158 |
| 2,812,880 | 11/1957 | Altman | 222/101 |
| 3,327,898 | 6/1967 | Farr | 73/864.11 |
| 3,579,303 | 5/1971 | Pickering | 422/72 |
| 4,195,526 | 4/1980 | Amos et al. | 73/864.11 |
| 4,210,026 | 7/1980 | Amos et al. | 73/864.11 |

Primary Examiner—Michael S. Marcus

[57] ABSTRACT

In the blood Bank area of a clinical laboratory a blood dispensing device is described capable of being used in conjunction with tubing containing blood which is attached to a blood donor bag. The end of said tubing is fed through one end of said device until it passes through the opposite end of the device at which point means are available to cut the tubing. The device is fitted with a knurled wheel or roller guided by an inclined track or ramp which upon turning the wheel in one direction causes the tubing to be squeezed or compressed thus allowing blood to be dispensed in a controlled dropwise fashion. In the opposite direction the wheel decompresses the tubing allowing it to be fed through once again in order to repeat the process as desired.

1 Claim, 2 Drawing Figures

BLOOD DISPENSER DEVICE

BACKGROUND OF INVENTION

In the past, it had been the convention, when cross-matching blood to determine compatibility of recipient and donor, that blood be taken with a pasteur pipet adapted with a bulb from a tube of blood attached to a donors blood bag and thereby to dispense said blood in a dropwise fashion. This tube of blood represented the donors blood and therefore was secured by tape to the donor bag and was identified as such by numbers coinciding with those appearing on the donor bag. It was found that some transfusion reactions were linked to incorrect indentification of this tube or the tube being placed on another bag accidentally. In view of this the American Association of Blood Banks and other concerned parties decided that a safer method of insuring correct blood sampling was to use the blood that was confined within the plastic tubing that was attached to the bag and had to definitely represent the donors blood. Blood is taken from a prospective blood donor using this plastic tubing about three feet in length, one end of which is permanently secured to the bag and the other end fitted with a needle. Using asceptic technique, vena puncture is made and blood is allowed to flow through the tubing by gravity into the bag until filled. At this point the tubing is clamped off near the needle and the tubing removed from the hub of the needle. Blood is then collected into a tube from the hub of the needle to be used for other donor testing such as syphilis, and hepatitis testing. The plastic tubing which had been previously clamped off so as to maintain a closed sterile system is then heat sealed along the length of the tubing at varying intervals two to four inches apart. This tubing commonly called the "sausage" is identified repetatively along its length by numbers coinciding with those on the bag. These numbers are put there by the manufacturer of the bag. During the compatibility testing, the technician cuts a segment of this tubing and squeezes it in order to dispense one or two drops of blood as needed. He then places the segment in a small tube which is attatched to the donor bag for future use.

This procedure has several drawbacks, namely, a scissors is needed to cut the tubing and repeatedly must be wiped clean since it is used to cut other segments representing different donors. Secondly, the tube containing the segment often falls to the ground and breaks due to improper securing to the bag. Thirdly, many technicians do not reuse the segment initially placed in the tube because they must check the number on said segment to insure proper identification. Often when the segment is cut the number has been partially cut as well. Consequently another segment is cut using the same procedure outlined, and often this segment is discarded rather than placing it in a tube etc.

The invention described herein eliminates the use of scissors, the need for a tube, and insures donor integrity. It can also cut down on the number of heat seals or segments heretofore needed along the length of the tubing.

SUMMARY OF INVENTION

In accordance with the present invention the device is attached to the tubing or "sausage link" by allowing one end of the tubing to be fed through a channel-like structure adapted with a wheel that rides on an inclined track or ramp. The wheel at one end of the device rides higher than at the other end whereat a means exists to cut the tubing. Consequently the tubing is "threaded" or fed through the channel at the point where the wheel rides highest with respect to the tubing which lies flat in said channel. The tubing is severed or cut at one end similar in fashion to a nail clip. The wheel is then rolled in the opposite direction where it continually compresses the tubing with increasing force thereby allowing blood to be squeezed out of the tubing at its severed end in a manner similar to a peristaltic pump. In this manner about four drops may be dispensed. If more blood is needed, the wheel is rolled in the opposite end whereby the tubing is decompressed while at the same time the blood is forced in that direction thus leaving a portion of the segment of tubing near the cutting end free from blood. The tubing may then be pushed forward and the empty segment cut off and discarded. Blood may then be dispensed by rolling the wheel as previously described.

DESCRIPTION OF INVENTION

Figure 1:
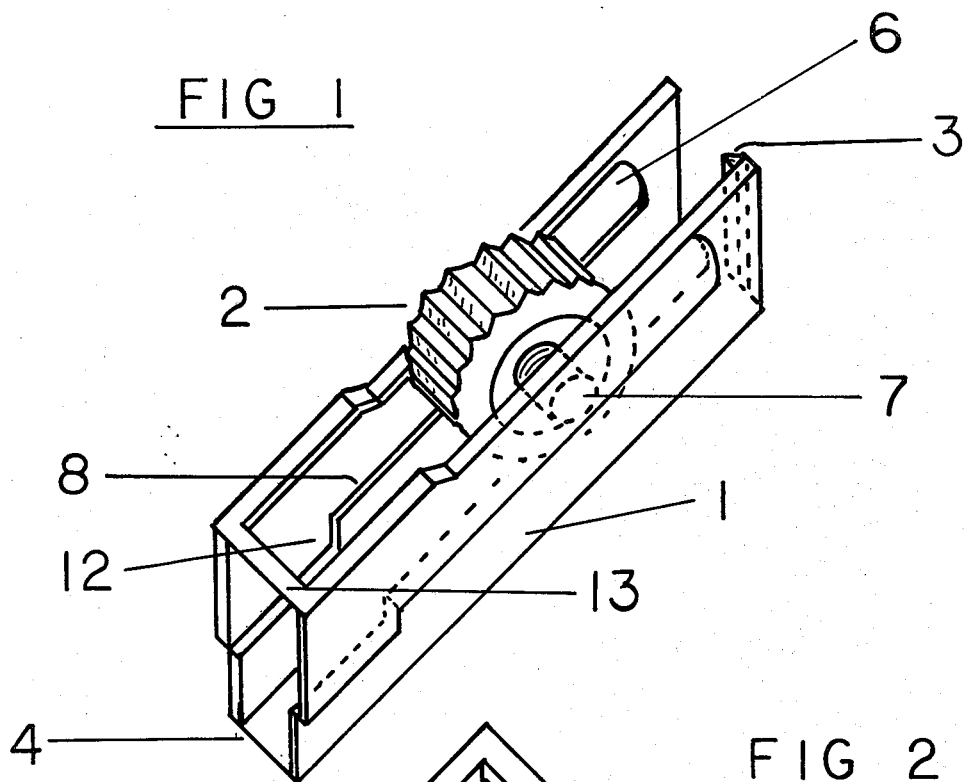
FIG. 1 is a partial cross-sectional view of the invention.
Figure 2:
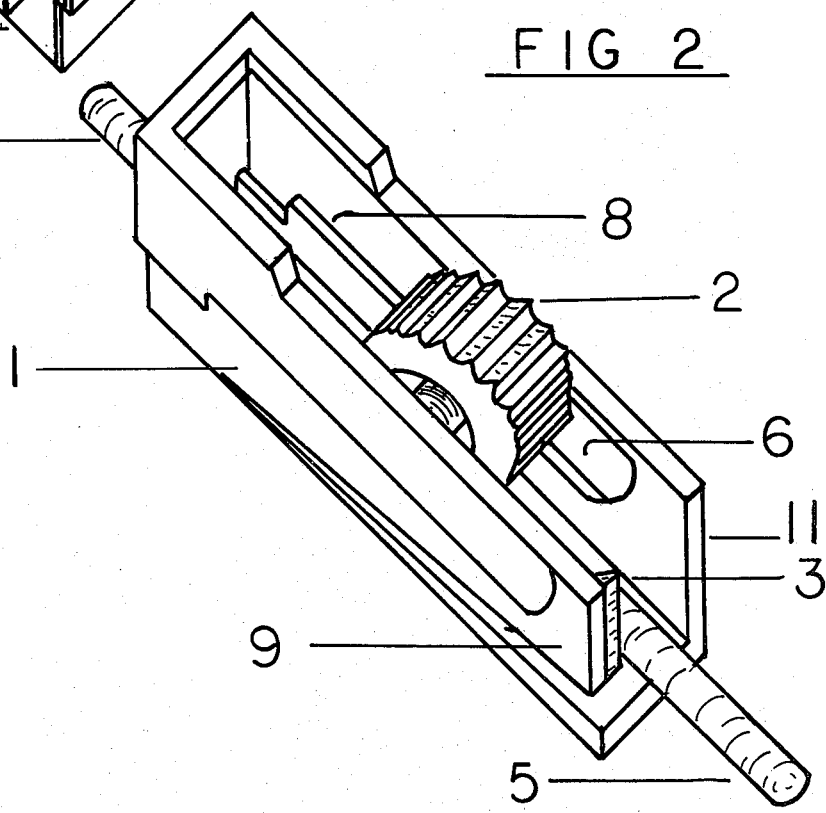
FIG. 2 gives another view of the invention in operation.

Referring to FIGS. 1 & 2 the invention 1, is shown to be constructed of two sides and a base 4 and of which house a wheel 2. The wheel is so constructed bearing at its center axis a supporting member or axle 7. This axle is seated within a notched member on either side of the walls respectively said notched member acting as a guide or track so as to allow the wheel to move freely in both directions. In essence the notched member 6 along with its bearing surface 8 act together to guide the wheel. The wheel may be rolled back until the axles drop the wheel to a lower position 12 relative to track 8. In this fashion the wheel is placed into the unit during manufacture and may be removed easily. It should be noted that in this position the wheel relative to base 4 is furthest apart from the base 4 of the device which runs the length of said device 1. The walls of the device 9 and 11 respectively are permanently affixed to base 4 along its length except towards the front of the device where cutting edge 3 is affixed. In other words at the point where the cutting blade is affixed to wall 9, this portion of the wall as well as the opposite wall 11 at that point may be moved as shown at 9 so as to activate the blade. Wall 11 is shown in its normal position when no cutting is required. It too can move as is shown at wall 9, and during the cutting process would be shown as in 9. At the front of the device where blade 3 is located on wall 9, the wheel is closest to base 4.

In operation the tubing 5 containing the blood would be inserted at the entry point where base 4 is shown. The wheel must assume its position towards the back of the device where it may drop down at point 12 on track 8. In this position the wheel is free to move up and down and allows tubing five to move freely beneath said wheel in order to feed it through so as to project itself at the front of the device bearing blade 3. If the wheel is in the middle of the device as shown in FIGS. 1 and 2 or towards the front where the cutting blade 3 is affixed, the tubing cannot pass beneath the wheel since said wheel at that point or points is closer to base 4 than at the other end. It must be remembered that base 4 is at an angle with wheel 2, or is like a ramp, the greatest distance apart being towards the back of the device ie towards 12 and the shortest distance between the wheel surface and base 4 is towards blade 3. In this manner, after tubing 5 has been inserted as shown in FIG. 2 the wheel is then moved towards blade 3 consequently compressing the tubing. If tubing 5 has not been cut or is yet sealed, ie heat sealed then it must be cut otherwise the compression caused by the wheel will merely allow the plastic tubing to bulge similar to a balloon. The tubing may be cut by placing thumb and forefinger one on wall 9 and 11 respectively, and compressing said walls in the direction of the tubing thus allowing blade 3 to sever the tubing. With this accomplished blood may be dispensed by rolling the wheel in the direction of the blade. It should be noted that the tubing should not be cut while the wheel is compressing it as this would cause the blood to squirt out. Ideally the wheel should be at the furthest end of the device away from the blade area. Then the tubing may be cut. When several drops of blood have been dispensed ie 3–4 drops, the wheel has moved furthest and can move no further. In this case the wheel is moved in the opposite direction, and as this is done, the blood at the end of the tubing is moved back also in the same direction of the wheel due to peristaltic action between said wheel and tubing. In this manner the tubing at the cutting end of the device is emptied of blood and allows the cutting of said tubing without messy blood spills etc. The invention described is a prefered embodiment. However the cutting aspects of the device may be changed in order to get the desired affect. Instead of the cutting edge being on a movable wall that operates in conjunction with its opposite moving wall, a blade which would be stationary could be secured over the two walls. Then one could simply raise the tubing up to the blade in order to cut it. The preferred embodiment seeks to eliminate touching the opened end of the tubing since some blood remains at the orifice and becomes slightly messy.

Note that in FIG. 2 tubing 5 is shown as a segment. Ideally the tubing enters through an entrance shown at base 4 ie the end away from the blade and the end of the tubing exits slightly at the blade end. The end of the tubing opposite to that where the blade is located is attached to the donors bag of blood and is affixed thereat permanently. As the tubing is cut and blood sample dispensed the device is moved closer to the end where the tubing is permanently affixed to the bag of blood. Due to the small quantity of blood required and the fact that the blood is either used or expires the length of tubing is sufficient for many tests and the device never gets close to the end of the tubing which is affixed to the donors blood. Ideally the tubing should only be heat sealed several times near the bag where it is a fixed and only once at the extreme opposite end. The reason for this is that sometimes the tubing will be so situated that one of the closed portions ie that which is crimped by heat sealing, will be in the device in approximately the middle and the wheel must be moved towards its furthest end (towards the blade) before its peristaltic action can move the blood. In this case one need only however remove the pressure on the tubing and guide it so that the crimped part of the tubing is at the cutting edge (blade section) or at the extreme opposite end towards the entrance point of the tubing 4. In other words if the tubing is heat sealed as described ie only in several places (extreme ends) there will be no problem of a crimped portion of tubing being placed or threaded through the device etc. Note FIGS. 1&2 cross-member 13 acts to support walls 9 and 11.

Having fully described my invention I claim:

1. A device for dispensing blood in a controlled, dropwise manner, said device comprising: a support means having a rectangularly shaped base member, a first upstanding vertical wall connected along a longitudinal edge to a longitudinal edge of said base member, a second upstanding vertical wall having first and second ends and having one of the longitudinal edges therebetween connected to the other longitudinal edge of said base member at said first end only whereby said second end is free to be displaced towards said first upstanding vertical wall, said upstanding vertical walls forming therebetween respective openings at the end of said support means to facilitate the placement of a blood conveying tube, each of said upstanding vertical walls having a notched surface extending along the longitudinal length thereof and forming a track or bearing surface, said track or bearing surface being of a stepped configuration so that the track or bearing surface has a substantial first portion, starting adjacent said second free end and at a first height above said base member and extends to said first end at a second lower height above said base member; a wheel member having a centrally located axle which axle is received in the notch and engages the track or bearing surface, said wheel member having circumferentially located grooves which are parallel to said axle; knife means connected to said second free end; and tube means located between said base member, vertical upstanding walls and wheel whereby blood may be dispensed in a controlled dropwise manner from said tube.

* * * * *